United States Patent [19]
Sato et al.

[11] Patent Number: 5,527,963
[45] Date of Patent: Jun. 18, 1996

[54] PRODUCTION OF N-VINYLFORMAMIDE

[75] Inventors: Shin-ichi Sato, Kitakyusyu; Yasuharu Mori, Yokohama; Toshimitsu Inoue, Kitakyusyu, all of Japan

[73] Assignee: Mitsubishi Chemical Corporation, Tokyo, Japan

[21] Appl. No.: 346,578

[22] Filed: Oct. 16, 1994

[51] Int. Cl.$^6$ .................................................. C07C 233/09
[52] U.S. Cl. .......................... 564/215; 564/187; 564/224
[58] Field of Search ...................................... 564/215, 159, 564/102, 224, 187

[56] References Cited

U.S. PATENT DOCUMENTS

| | | | |
|---|---|---|---|
| 3,914,304 | 10/1975 | Schnabel et al. | 260/561 R |
| 4,490,557 | 12/1984 | Dawson et al. | 564/159 |

FOREIGN PATENT DOCUMENTS 0184074  6/1986  European Pat. Off. .

OTHER PUBLICATIONS

Abstract of Japanese Application No. 5-301851 1993.
Abstract of Japanese Application No. 3-181451 1991.
Abstract of Japanese Application No. 3-181452 1991.

*Primary Examiner*—Shailendra Kumar
*Attorney, Agent, or Firm*—David G. Conlin; Peter F. Corless

[57] ABSTRACT

An improved process for producing N-vinylformamide including the steps of evaporating N-(α-substituted-ethyl)formamide or ethylidenebisformamide under reduced pressure and thermally decomposing the vapor at 150°–600° C., wherein the improvement comprises performing thermal decomposition by means of a pyrolysis reactor which is made up of two stages, the first being an unpacked tubular reactor constructed such that liquid flows down and the second being a packed tubular reactor, while keeping the vapor temperature at 200°–400° C. at the outlet of the unpacked tubular reactor and the inside temperature of the packed tubular reactor at 200°–600° C.

14 Claims, 1 Drawing Sheet

PRODUCTION OF N-VINYLFORMAMIDE

BACKGROUND OF THE INVENTION

1. Field of the Invention

The present invention relates to a process for producing N-vinylformamide and, more particularly, to a process for producing N-vinylformamide by generating N-(αsubstituted-ethyl)formamide vapor or ethylidenebisformamide vapor by evaporation under reduced pressure and thermally decomposing the vapor at 150°–600° C. in a reactor.

2. Description of the Prior Art

N-vinylformamide is important as a polymerizable monomer for a water-soluble polymer which finds use as a flocculant. According to a known process, it is produced by thermal decomposition in vapor phase of N-(α-alkoxyethyl)formamide, N-(α-cyanoethyl)formamide, or ethylidenebisformamide. To be more specific, the thermal decomposition involves the steps of evaporating the above-mentioned starting material by heating, subjecting the vapor to thermal decomposition at 300°–600° C. in a packed or unpacked tubular reactor, and cooling the pyrolysis gas. (U.S. Pat. No. 3,914,304 and European Patent Laid-Open No. 184074) However, thermal decomposition in this conventional process tends to deposit tarry or solid resinous substances on the packing or wall of the tubular reactor. In an extreme case, they clog the reactor, hindering stable operation.

In order to avoid the deposition of resinous substances, the present inventors had previously proposed a pyrolysis reactor made up of two stages, the first being an unpacked tubular reactor and the second being a packed tubular reactor. (Japanese Patent Laid-Open No. 181451/991) This reactor functions satisfactorily (without deposition of resinous substances) in an experimental scale so long as it is small enough for the starting material to be heated rapidly; however, it does not in an industrial scale in which the rapid heating of the starting material is difficult. A possible way of overcoming this disadvantage is by extending the residence time of the starting material in the reactor or intensifying the heating of the reactor. However, it is unfavorable for productivity and energy consumption.

In view of the foregoing, the present inventors carried out a series of researches on how to prevent the deposition of resinous substances in the tubular reactor. As the result, it was found that the object is achieved by operating a composite reactor of specific structure at a specific pyrolysis temperature. This finding led to the present invention.

SUMMARY OF THE INVENTION

The gist of the present invention resides in an improved process for producing N-vinylformamide including the steps of evaporating N-(α-substituted-ethyl)formamide or ethylidenebisformamide under reduced pressure and thermally decomposing the vapor at 150°–600° C., wherein the improvement comprises performing thermal decomposition by means of a pyrolysis reactor which is made up of two stages, the first being an unpacked tubular reactor constructed such that liquid flows down and the second being a packed tubular reactor, while keeping the vapor temperature at 200°–400° C. at the outlet of the unpacked tubular reactor and the inside temperature of the packed tubular reactor at 200°–600° C.

DESCRIPTION OF THE PREFERRED EMBODIMENTS

Figure 1:
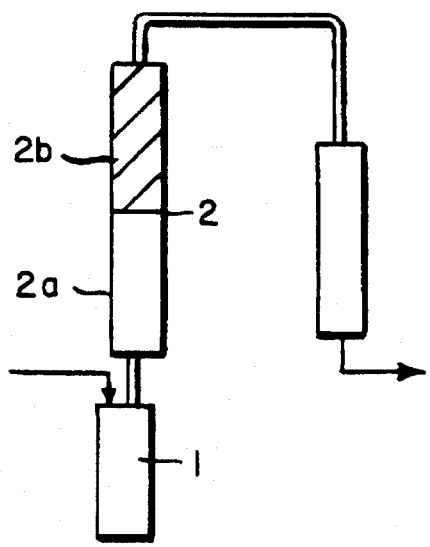
FIG. 1 is a schematic diagram showing the experimental arrangements used in Examples 1 to 3 and Comparative Example 1.

A detailed description of the invention follows. The process of the present invention employs as the starting material N-(α-substituted-ethyl)formamide, with the α-substituent on the ethyl group including lower alkoxyl groups (such as methoxy group, ethoxy group, n-propoxy group, isopropoxy group, n-butoxy group, s-butoxy group, and t-butoxy group) and cyano group. Those having higher alkoxyl groups as the α-substituent are undesirable although usable, because they do not evaporate readily.

The thermal decomposition of N-(α-substitutedethyl)formamide yields N-vinylformamide and alcohol (if the α-substituent is an alkoxyl group) or hydrogen cyanide (if the α-substituent is a cyano group) as a by-product. Also, the thermal decomposition of ethylidenebisformamide yields N-vinylformamide and formamide as a by-product.

According to the present invention, the starting material is first evaporated by heating at 80°–210° C. under reduced pressure (3–600 Torr). The resulting vapor is immediately introduced into the tubular reactor specified in the present invention. The vapor flows upward through the reactor for thermal decomposition.

According to the present invention, it is essential that the tubular reactor for thermal decomposition be made up of two stages, the first being an unpacked tubular reactor constructed such that liquid flows down and the second being a packed tubular reactor. To meet this requirement, the unpacked tubular reactor (for the first stage) should be installed almost vertical or slightly aslant so that liquid flows down therein. The angle of permissible inclination is greater than 45 degrees, preferably greater than 60 degrees, depending on the diameter and length of the tubular reactor. By contrast, the packed tubular reactor (for the second stage) may be installed either horizontal or vertical. The vapor of the starting material is admitted into the first tubular reactor through its lower inlet and the reaction gas is discharged through its upper outlet. The reaction gas is subsequently introduced into the second tubular reactor.

The first and second tubular reactors may vary in volume such that their ratio ranges from 1:9 to 9:1. The packings for the packed tubular reactor may be glass or stainless steel spheres (3–12 mm in diameter) or glass or stainless steel Raschig rings (5–15 mm in diameter). The packings should be held by closing the end of the reactor with a metal net in the usual manner.

The tubular reactor may be of single-tube type or multiple-tube type or their combination type. The diameter of the tube is not specifically restricted so long as it is large enough for the gas mixture to be heated to and kept at a desired temperature. This is true particularly for the first tubular reactor because the thermal decomposition is an endothermic reaction. The reactor does not need to be a purpose-built one; it may be a so-called pipe reactor made up of ordinary pipes. The unpacked tubular reactor may be a pipe reactor and the packed tubular reactor that follows may be of multiple pipe type.

The pyrolysis reactor may be so constructed as to assume an appearance of a single reactor (composite tubular reactor) in which the first and second stages are integrated. However, this is not always necessary. The reactor may be constructed of an unpacked single-tube reactor of vertical type (for the first stage) and a packed multiple-pipe reactor (for the second stage). In this case, the first and second reactors may differ from each other in outside diameter. Alternatively, it is also possible to connect two independently designed reactors to each other, one being an unpacked reactor of vertical type and the other being a packed reactor. The connecting part should be kept at a higher temperature than the unpacked reactor so as to avoid the deposition of resinous substances thereon.

In order to maintain the pyrolysis temperature of 150°–600° C. specified in the present invention, it is necessary to heat the tubular reactor externally. Heating may be accomplished by the aid of electric heater (wire or plate), steam, oil, or molten inorganic salt. The reaction pressure may be the same as the evaporation pressure. The residence time of vapor in the reactor is usually 0.1–5 seconds.

According to the present invention, the thermal decomposition partly takes place in the first stage and goes to completion in the second stage.

For thermal decomposition, the unpacked reactor (in the first stage) should be heated to 200°–450° C. so that the vapor temperature at its outlet is 200°–400° C., preferably 240°–360° C. Raising the vapor temperature above 400° C. involves some difficulty in the case of large-scale reactor and increases the energy cost. If the vapor temperature is lower than 200° C., resinous substances will deposit on the reactor wall, decreasing the yield of N-vinylformamide.

The temperature of the packed reactor (in the second stage) should be 200°–600° C. preferably 350°–500° C., which is higher than the vapor temperature at the outlet of the unpacked reactor (in the first stage). This is because higher temperatures are favorable for the complete thermal decomposition of unreacted matters coming from the first stage. On the other hand, excessively high temperatures above 600° C. cause side reactions which decompose the desired N-vinylformamide to lower its yield.

Incidentally, the temperature of the tubular reactor means the temperature of the inner wall of the reactor, and the vapor temperature at the outlet of the unpacked reactor is measured at the center of the outlet of the tubular reactor.

According to the present invention, N-(α-substituted-ethyl)formamide or ethylidenebisformamide (as the starting material) is heated and evaporated under reduced pressure in an evaporator and the resulting vapor is immediately introduced into the above-mentioned reactor in which thermal decomposition takes place. Subsequently, the gas produced by thermal decomposition is cooled to condense and recover a mixture of N-vinylformamide, by-products, and a small amount of unreacted starting material. It is desirable that after evaporation by the evaporator, the vapor of the starting material be immediately introduced into the vertical unpacked reactor (as the first stage for thermal decomposition) kept at 150°–600° C. The mixture recovered after condensation may be distilled, if necessary, to separate N-vinylformamide.

According to the present invention, it is possible to prevent the deposition of resinous substance on the reactor wall. A probable reason for this is as follows: It is known that N-vinylformamide resulting from thermal decomposition partly gives rise to high-boiling byproducts through dimerization if the reactor temperature is lower than 200° C. but the by-products are decomposed again into N-vinylformamide if the reactor temperature is higher than 200° C. On the other hand, the reactor wall temperature tends to decrease if there is no sufficient heating because the thermal decomposition is an endothermic reaction. This temperature decrease leads to the deposition of resinous substances. The unpacked reactor in the first stage maintains the desired wall temperature comparatively easily because it prevents the abrupt thermal decomposition. Nevertheless, it permits the deposition of a small amount of resinous substances. In the case of horizontal unpacked reactor, the high boiling by-products deposit on the reactor wall and the deposit turns into resinous substances. However, this is not the case for the vertical unpacked reactor used in the present invention. In it liquid flows downward and hence high-boiling substances do not stay long on the reactor wall but flow down to the still and eventually discharged from the system. Even though a small amount of high-boiling substances deposit in the form of droplets on the reactor wall, they would evaporate and decompose again readily, leaving no resinous substances. In addition, the effect of endothermic reaction which lowers the temperature of the packed reactor (in the second stage) and the packings therein is lessened because the reactants enter the packed reactor after partial reaction and they undergo thermal decomposition completely therein.

The following examples are included merely to aid in the understanding of the present invention, and variations may be made by one skilled in the art without departing from the spirit and scope of the invention.

Example 1

This example was practiced using the apparatus as shown in FIG. 1. N-(α-methoxyethyl)formamide was evaporated at a rate of 2 kg/h at 178° C. under reduced pressure (120 Torr) using the evaporator of wetted wall type (1). The vapor was immediately introduced into the reactors (2a, 2b) sequentially for thermal decomposition. The reactor (2a) is an unpacked one, 40 mm in diameter and 1 m long. The reactor (2b) is a packed one, 40 mm in diameter and 1 m long, containing stainless steel Raschig rings (6 mm in diameter). Both reactors are equipped with external electric heaters, and the heating temperature is shown in Table 1. The pyrolysis gas was cooled to 15° C. for condensation by the cooler. Thus there was obtained a mixture containing N-vinylformamide. The above-mentioned process for thermal decomposition was carried out continuously for 100 hours. Finally, the apparatus was disassembled to determine the amount of resinous substances which had deposited on the inner wall of the reactor. Table 1 shows the conditions for thermal decomposition, the yield of N-vinylformamide, and the amount of resinous substances.

Examples 2 and 3 and Comparative Example 1

The same procedure as in Example 1 was repeated except that the heating temperature of the unpacked reactor was changed. The results are shown in Table 1. Examples 4 to 6 and Comparative Example 2

Figure 2:
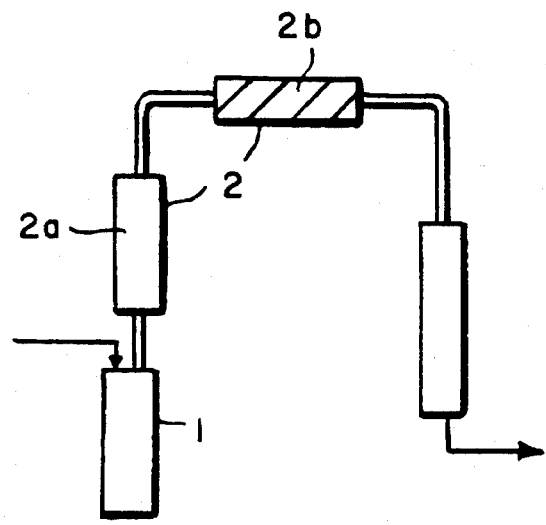
FIG. 2 is a schematic diagram showing the experimental arrangements used in Examples 4 to 6 and Comparative Example 2.

These examples were practiced using the apparatus shown in FIG. 2. It is the same in size as that used in Example 1 except that the packed reactor is installed horizontal. The same procedure as in Example 1 was repeated except that the heating temperature of the unpacked reactor was changed. The results are shown in Table 1.

Comparative Examples 3 to 6

Figure 3:
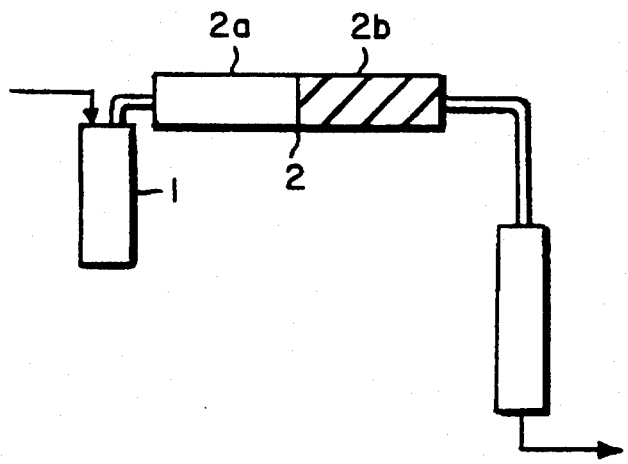
FIG. 3 is a schematic diagram showing the experimental arrangements used in Comparative Examples 3 to 6.

These examples were practiced using the apparatus shown in FIG. 3. It is the same in size as that used in Example 1 except that both reactors are installed horizontal. The same procedure as in Example 1 was repeated except that the heating temperature of the unpacked reactor was changed. The results are shown in Table 1.

TABLE 1

| | Apparatus | Temperature in unpacked reactor (°C.) | Temperature at outlet of unpacked reactor (°C.) | Temperature in packed reactor (°C.) | Duration of operation (h) | Amount of resinous substances in reactor (g) | Yield of N-vinyl-formamide (%) |
|---|---|---|---|---|---|---|---|
| Example 1 | FIG. 1 | 400 | 340 | 450 | 100 | 0 | 94 |
| Example 2 | FIG. 1 | 350 | 300 | 450 | 100 | 0 | 94 |
| Example 3 | FIG. 1 | 280 | 250 | 450 | 100 | 0 | 93 |
| Example 4 | FIG. 2 | 400 | 340 | 450 | 100 | 0 | 94 |
| Example 5 | FIG. 2 | 350 | 300 | 450 | 100 | 0 | 94 |
| Example 6 | FIG. 2 | 280 | 250 | 450 | 100 | 0 | 93 |
| Comparative Example 1 | FIG. 1 | 180 | 180 | 450 | 100 | 0.2 | 92 |
| Comparative Example 2 | FIG. 2 | 180 | 180 | 450 | 100 | 0.5 | 92 |
| Comparative Example 3 | FIG. 3 | 400 | 340 | 450 | 100 | 0.2 | 94 |
| Comparative Example 4 | FIG. 3 | 350 | 300 | 450 | 100 | 0.2 | 94 |
| Comparative Example 5 | FIG. 3 | 280 | 250 | 450 | 100 | 4 | 93 |
| Comparative Example 6 | FIG. 3 | 180 | 180 | 450 | 24 | 12 | 92 |

EFFECT OF THE INVENTION

The process of the present invention can be favorably applied to the stable industrial mass production of N-vinyl-formamide in high yields because it prevents the deposition of resinous substances in the pyrolysis reactors.

What is claimed is:

1. A process for producing N-vinylformamide including the steps of evaporating N-(α-substituted ethyl)formamide or ethylidenebisformamide under reduced pressure and thermally decomposing the vapor at 150°–600° C., the process comprising:

performing thermal decomposition of evaporated N-(α-substituted ethyl)formamide or ethylidenebisformamide under reduced pressure with a pyrolysis reactor which is made up of two stages, the first being an unpacked tubular reactor constructed such that liquid flows down and the second being a packed tubular reactor, while keeping the vapor temperature at 200°–400° C. at the outlet of the unpacked tubular reactor and the inside temperature of the packed tubular reactor at 200°–600° C.

2. A process as defined in claim 1, wherein the N-(α-substituted-ethyl)formamide is N-(α-cyanoethyl)formamide.

3. A process as defined in claim 1, wherein the N-(α-substituted-ethyl)formamide is N-(α-lower alkoxyethyl)formamide.

4. A process as defined in claim 1, wherein the N-(α-substituted-ethyl)formamide is N-(α-methoxyethyl)formamide.

5. A process as defined in claim 1, wherein the N-(α-substituted-ethyl)formamide or ethylidenebisformamide is evaporated at 3–600 Torr and 80°–210° C.

6. A process as defined in claim 1, wherein the first stage of the pyrolysis reactor is a vertical unpacked tubular reactor.

7. A process as defined in claim 1, wherein the first stage of the pyrolysis reactor is an inclined unpacked tubular reactor.

8. A process as defined in claim 7, wherein the angle of inclination is greater than 45 degrees with respect to the horizontal.

9. A process as defined in claim 7, wherein the angle of inclination is greater than 60 degrees with respect to the horizontal.

10. A process as defined in claim 1, wherein the packed tubular reactor is of vertical type.

11. A process as defined in claim 1, wherein the unpacked tubular reactor and packed tubular reactor vary in volume such that their ratio ranges from 1:9 to 9:1.

12. A process as defined in claim 1, wherein the packings in the packed tubular reactor are spheres or Raschig rings.

13. A process as defined in claim 1, wherein the unpacked tubular reactor is heated such that the vapor temperature at its outlet is 240°–360° C.

14. A process as defined in claim 1, wherein the packed tubular reactor is kept at 350°–500° C.

* * * * *